United States Patent
Dailey et al.

(10) Patent No.: US 10,678,338 B2
(45) Date of Patent: Jun. 9, 2020

(54) DETERMINING AND EVALUATING DATA REPRESENTING AN ACTION TO BE PERFORMED BY A ROBOT

(71) Applicant: AT&T Intellectual Property I, L.P., Atlanta, GA (US)

(72) Inventors: Robert Dailey, Austin, TX (US); Eric Zavesky, Austin, TX (US); James Pratt, Round Rock, TX (US); Yupeng Jia, Austin, TX (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 224 days.

(21) Appl. No.: 15/619,265

(22) Filed: Jun. 9, 2017

(65) Prior Publication Data
US 2018/0356895 A1  Dec. 13, 2018

(51) Int. Cl.
| | | |
|---|---|---|
| G06F 3/01 | (2006.01) | |
| A61B 34/30 | (2016.01) | |
| A61B 17/00 | (2006.01) | |
| B25J 13/08 | (2006.01) | |
| A61B 34/00 | (2016.01) | |

(52) U.S. Cl.
CPC ............ *G06F 3/017* (2013.01); *A61B 34/30* (2016.02); *A61B 34/77* (2016.02); *B25J 13/08* (2013.01); *G06F 3/011* (2013.01); *A61B 2017/00207* (2013.01); *G05B 2219/35444* (2013.01); *G05B 2219/40413* (2013.01); *G06F 2203/0383* (2013.01); *Y10S 901/09* (2013.01)

(58) Field of Classification Search
CPC ........... G06F 3/017; G06F 3/011; B25J 13/08; Y10S 901/09; G05B 2219/35444; G05B 2219/40413

USPC .................................................. 700/245, 258
See application file for complete search history.

(56) References Cited

U.S. PATENT DOCUMENTS

| | | | | |
|---|---|---|---|---|
| 6,493,606 B2 * | 12/2002 | Saijo | ........................ | B25J 13/00 318/568.1 |
| 7,113,848 B2 * | 9/2006 | Hanson | .................. | G06N 3/008 700/245 |
| 7,515,992 B2 * | 4/2009 | Sawada | .................. | G06N 3/008 318/568.11 |

(Continued)

FOREIGN PATENT DOCUMENTS

| | | |
|---|---|---|
| WO | 2005088539 A2 | 9/2005 |
| WO | 2015192117 A1 | 12/2015 |
| WO | 2016133644 A1 | 8/2016 |

OTHER PUBLICATIONS

Wachs, J. P. et al., "Vison-based hand-gesture applications," Communications of the ACM, vol. 54, Issue 2, Feb. 2011, pp. 60-71.

(Continued)

*Primary Examiner* — Jaime Figueroa
(74) *Attorney, Agent, or Firm* — Baker Botts, LLP (57) ABSTRACT

In one embodiment, a processor accesses sensor input data received from one or more sensors. The sensor input data represents one or more gestures. The processor determines, based on the sensor input data representing the one or more gestures, action data representing an action to be performed by a robot. The action includes physical movements of the robot. The processor evaluates the action data representing the action to be performed by the robot in light of evaluation data.

20 Claims, 5 Drawing Sheets

(56) References Cited

U.S. PATENT DOCUMENTS

| | | | |
|---|---|---|---|
| 8,046,313 B2 | 10/2011 | Hoffberg et al. | |
| 8,147,503 B2 | 4/2012 | Zhao et al. | |
| 8,391,954 B2 | 3/2013 | Quaid, III | |
| 8,543,240 B2* | 9/2013 | Itkowitz | G06F 3/014 414/2 |
| 8,880,222 B2* | 11/2014 | Kawamoto | B25J 9/1664 318/568.12 |
| 8,909,370 B2* | 12/2014 | Stiehl | B25J 9/1671 700/245 |
| 8,935,006 B2* | 1/2015 | Vu | B25J 5/007 700/264 |
| 8,942,849 B2* | 1/2015 | Maisonnier | B25J 11/0005 700/250 |
| 9,044,863 B2* | 6/2015 | Mead | B25J 9/1697 |
| 9,052,710 B1* | 6/2015 | Farwell | G05B 19/423 |
| 9,079,313 B2* | 7/2015 | Olivier, III | B25J 9/1689 |
| 9,105,207 B2 | 8/2015 | Leung | |
| 9,221,170 B2* | 12/2015 | Barajas | B25J 9/1664 |
| 9,283,675 B2 | 3/2016 | Hager et al. | |
| 9,358,685 B2* | 6/2016 | Meier | B25J 9/1602 |
| 9,375,845 B1* | 6/2016 | Annan | B25J 11/0005 |
| 9,387,587 B2* | 7/2016 | Som | B25J 9/1656 |
| 9,492,241 B2 | 11/2016 | Joskowicz et al. | |
| RE46,310 E* | 2/2017 | Hoffberg | G06F 3/0482 |
| 9,753,453 B2* | 9/2017 | Benaim | G06K 9/00355 |
| 9,811,074 B1* | 11/2017 | Aichele | G05B 19/4069 |
| 9,956,687 B2* | 5/2018 | Florencio | B25J 9/1694 |
| 9,975,243 B2* | 5/2018 | Erhart | G05B 19/4187 |
| 10,144,135 B2* | 12/2018 | Le Borgne | B25J 9/1694 |
| 10,166,673 B2* | 1/2019 | Orman | G06F 3/0346 |
| 2010/0164950 A1* | 7/2010 | Zhao | G06T 11/00 345/419 |
| 2011/0118753 A1* | 5/2011 | Itkowitz | G06F 3/014 606/130 |
| 2014/0046128 A1 | 2/2014 | Lee et al. | |
| 2014/0058407 A1 | 2/2014 | Tsekos et al. | |
| 2014/0204190 A1 | 7/2014 | Rosenblatt, III et al. | |
| 2014/0287393 A1 | 9/2014 | Kumar et al. | |
| 2014/0378995 A1 | 12/2014 | Kumar et al. | |
| 2015/0062168 A1 | 3/2015 | Ng-Thow-Hing et al. | |
| 2015/0217449 A1* | 8/2015 | Meier | B25J 9/1602 700/257 |
| 2015/0358614 A1 | 12/2015 | Jin | |
| 2015/0366628 A1 | 12/2015 | Ingmanson | |
| 2016/0109954 A1* | 4/2016 | Harris | G06F 3/017 345/156 |
| 2016/0143693 A1 | 5/2016 | Yilmaz et al. | |
| 2016/0225192 A1 | 8/2016 | Jones et al. | |
| 2016/0249989 A1 | 9/2016 | Devam et al. | |
| 2016/0324598 A1 | 11/2016 | Bothorel et al. | |
| 2016/0331464 A1 | 11/2016 | Ecabert et al. | |
| 2017/0049524 A1 | 2/2017 | Olson | |
| 2017/0056115 A1 | 3/2017 | Corndorf et al. | |

OTHER PUBLICATIONS

Jung, S., "Augmented Reality Surgery: How a Mobile Device Can Save Your Life," https://iq.intel.com/how-a-mobile-device-can-save-your-life-augmented-reality-surger/, Apr. 16, 2014, 8 pages.

Bleser, G. et al., "Cognitive Learning, Monitoring, and Assistance of Industrial Workflows Using Egocentric Sensor Networks," PLOS One, Jun. 30, 2015, pp. 1-41.

\* cited by examiner

DETERMINING AND EVALUATING DATA REPRESENTING AN ACTION TO BE PERFORMED BY A ROBOT

BACKGROUND

Humans use machines, such as robots, to perform a variety of tasks. For example, humans may use machines, such as robots, to perform certain physical tasks. The task performed by the machine could include, for example, assisting the human in performing a task or performing the task in place of the human.

SUMMARY OF PARTICULAR EMBODIMENTS

In one embodiment, a processor accesses sensor input data received from one or more sensors. The sensor input data represents one or more gestures. The processor determines, based on the sensor input data representing the one or more gestures, action data representing an action to be performed by a robot. The action includes physical movements of the robot. The processor evaluates the action data representing the action to be performed by the robot in light of evaluation data.

Other aspects of the present disclosure will be readily apparent to one skilled in the art from the following figures, descriptions, and claims.

BRIEF DESCRIPTION OF THE DRAWINGS

To assist in understanding the present disclosure, reference is now made to the following description taken in conjunction with the accompanying drawings, in which.

DESCRIPTION OF EXAMPLE EMBODIMENTS

The disclosed system may improve accuracy of one or more technical activities through machine-guided movements. Technical operations may be optimized by mapping actions to be performed by a robot (e.g., making an incision or cracking ribs) to one or more macro gestures (e.g., a slicing or jabbing gesture) of a user (e.g., a surgeon). As an example, a surgeon may perform one or more gestures such as circling or sweeping his wrist to start a robotic process such as a medical procedure. The gestures may be synchronized with the procedure's timeline (e.g., a medical procedure's timeline) to automatically begin, navigate, and observe the process. Mapping simple gestures performed by a user to minute and detailed actions to be performed by a robot may reduce the requirement of the user (e.g., a surgeon) to perform the minute and detailed interactions, which may in turn reduce or eliminate user mistakes. For example, a surgeon performing heart surgery may be required to move a heart one millimeter. In certain circumstances, due to lack of sleep, tremors, or lack of hand-eye control, the surgeon may accidentally move the heart two millimeters, causing irreparable damage to the patient. In the disclosed system, a surgeon's gesture of moving his hand one inch may be mapped to an action to be performed by a robot of moving a heart one millimeter, which may reduce or avoid accidental movement that may occur with direct interaction methods.

Machine learning (ML) is the general practice of mathematical and statistical methods concerned with learning parameters for an algorithm from repeated examples to generate a repeatable response. Artificial intelligence (AI) is a superset of ML concerned with demonstrating intelligence through machines by combining ML and feedback observation systems. One example of AI is teaching a machine, such as a robot, to learn to perform a task without being explicitly programmed to do so. For example, one or more components of a machine, or one or more components associated with the machine, may study data to make predictions on the data based on pattern recognition. AI and ML may play an important role in technical activities such as surgery, technical repairs, and manufacturing. Surgery involving complex technical procedures, for example, may require precise interactions with a patient. Bypass surgery (e.g., coronary artery bypass surgery) may require several complex but well-defined actions, such as making an incision in a patient's chest, cracking ribs, finding a particular artery, and isolating the heart. The disclosed system may have AI and ML abilities that determine and evaluate data representing an action to be performed by a robot so that procedures requiring a high level of precision, such as heart surgery, are automated. For example, a surgeon may make a series of broad gestures to instruct a robot do perform heart surgery, and the robot may possess the skills and knowledge to specifically perform one or more precise actions associated with these broad gestures.

The use of virtual reality (VR) and/or augmented reality (AR) technology offers situational awareness that a user, such as a surgeon, may not otherwise possess. For example, the system may include a computer with a VR/AR display that displays and highlights a repair site (e.g., an artery or a fiber optic cable). An operator of the computer may verify that the highlighted repair site (e.g., the artery) is the correct repair site and issue a set of simple gestures to repair (e.g., stitch together) the repair site, such as simple twisting gestures and/or an audible command. The robot may then proceed to execute a precisely articulated, human driven operation with real-time feedback (e.g. speed and orientation control).

As another example of increased situational awareness of the disclosed system over situational awareness of a user (e.g., a surgeon) performing an activity, the disclosed system may maintain the status of progress and tasks in queue to retain robotic actions being performed. The system may track observations (e.g., vital signs) in real time to provide situational awareness to the operator of the system. For example, a system that includes a robot performing a complex operation requiring a high level of detail can record a force required to complete a process and compare the force to a typical force in a similar operation based on historical data. Notifications and suggestions may be sent back to an operator of the system to non-intrusively introduce conditions observed during the operation. When a condition unfamiliar to the operator is detected, the low-latency system may cross-reference and visually overlay observations on a VR/AR display from other historical procedures.

Figure 1:
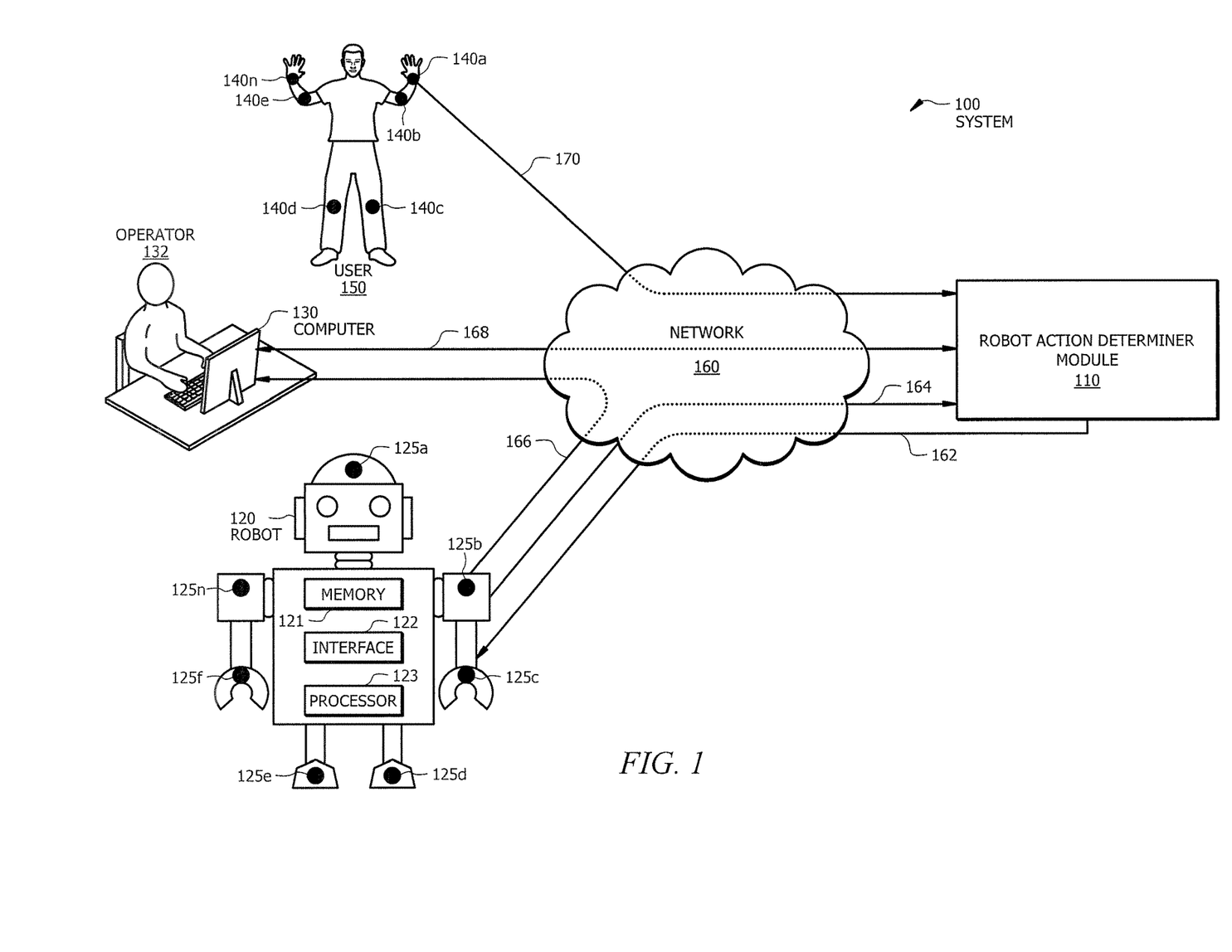
FIG. 1 illustrates an example of a system for determining and evaluating data representing an action to be performed by a robot, according to certain embodiments.

FIG. 1 illustrates an example of a system 100 for determining and evaluating data representing an action to be performed by a robot, according to certain embodiments. As illustrated in FIG. 1, system 100 includes a robot action determiner module 110, a robot 120, a computer 130, one or more user sensors 140 associated with (e.g., worn by) a user 150, and a network 160. In general, system 100 facilitates accessing, by robot action determiner module 110, data received from user sensors 140 of user 150 and, based on the accessed data, determining and evaluating, by robot action determiner module 110, action data representing an action to be performed by robot 120.

System 100 or portions thereof may be associated with an entity, which may include any entity, such as a business or company (e.g., a healthcare provider or a telecommunications company), that desires to make use of robot 120 to perform certain actions and to use system 100 to determine and evaluate data representing actions to be performed by robot 120. Throughout this description, this entity is referred to as the entity associated with system 100. For example purposes only, this description focuses on an embodiment in which the entity is a health care provider (e.g., a hospital) and user 150 is a surgeon; however, the present disclosure contemplates the entity being any suitable type of entity and user 150 being any suitable user. In one embodiment, robot action determiner module 110, robot 120, computer 130, and user sensor(s) 140 may be operated by the entity and connected by network 160; however, the present disclosure contemplates all or a portion of system 100 being operated by any other suitable entity. The elements of system 100 may be implemented using any suitable combination of hardware, firmware, and software.

In the illustrated embodiment, robot action determiner module 110 of system 100 is a computer module for determining and evaluating data representing an action to be performed by robot 120. In certain embodiments, robot action determiner module 110 accesses information such as sensor input data from user sensor(s) 140. The sensor input data may represent one or more gestures performed by user 150, such as a swipe, a jab, an uppercut, a circular hand movement, a twisting hand movement, a throw, and/or any other suitable gesture. Robot action determiner module 110 may determine, based on the sensor input data, action data representing an action (e.g., cutting an incision or cracking a rib) to be performed by robot 120 of system 100. For example, robot action determiner module 110 may determine action data by mapping the one or more gestures performed by user 150 (e.g., a jab) to an action (e.g., cracking a sternum during open heart surgery). In certain embodiments, the action data determined and evaluated by robot action determiner module 110 represents a pre-defined set of movements to be performed by robot 120. The pre-defined set of movements may include a single movement (e.g., sewing one stitch), a series of repeated movements (e.g., sewing multiple stitches), and/or a series of different movements (e.g., cutting an incision in a patient's chest, cutting the patient's breastbone, and repairing a blocked artery).

Robot action determiner module 110 may have AI and ML capabilities. For example, robot action determiner module 110 may study evaluation data to make predictions for action data. In certain embodiments, robot action determiner module 110 evaluates the action data representing the action to be performed by robot 120 in light of evaluation data. For example, robot action determiner module 110 may evaluate action data representing cracking a sternum during open heart surgery in light of historical data of past open heart surgery procedures that involved cracking a sternum. In certain embodiments, robot action determiner module 110 may discover similarities between the action data (e.g., action data representing cracking a sternum) and the evaluation data (e.g., historical data) and, based on these similarities, transmit the action data to robot 120 via network 160 (see notation 162 of FIG. 1). In some embodiments, robot action determiner module 110 may discover differences between the action data and the evaluation data and, based on these differences, alter the action data to more closely align with the evaluation data and/or transmit the action data to an operator (e.g., operator 132) of system 100 for feedback. Robot action determiner module 110 is described in more detail below in reference to FIG. 2.

Robot 120 of system 100 may be any machine that can perform one or more actions automatically. For example, robot 120 may be a medical robot (e.g., a surgical robot) or an industrial robot. Robot 120 may perform one or more actions including but not limited to moving (e.g., moving in multiple axes), cutting (e.g., cutting an artery or a wire), breaking (e.g., breaking a bone or a rock), inspecting (e.g., inspecting a heart or a fiber optic hub), testing (testing an environmental condition), repairing (e.g., repairing a wound), and/or any other suitable action. In some embodiments, robot 120 performs an action or a series of actions in accordance with action data received from robot action determiner module 110. For example, robot 120 may perform a precise action such as sewing up a patient's wound with one stitch. As another example, robot 120 may perform a series of precise actions such as sewing up a patient's wound with ten stitches. As still another example, robot 120 may perform a series of actions that include different movements such as moving one millimeter forward, two millimeters to the right, and then sewing up a patient's wound with seven stitches.

Robot 120 includes a memory 121, an interface 122, and a processor 123. Memory 121 of robot action determiner module 110 stores, permanently and/or temporarily, received and transmitted information, as well as system software, control software, and other software for robot 120, and a variety of other information. Memory 121 may store information for execution by processor 123. In the illustrated embodiment, memory 121 stores data (e.g., action data) received from robot action determiner module 110. Memory 121 of robot 120 may store data received from computer 130, sensor(s) 125 of robot 120, and/or user sensor(s) 140 of user 150.

Memory 121 includes any one or a combination of volatile or non-volatile local or remote devices suitable for storing information. For example, memory 121 may include Random Access Memory ("RAM"), Read-only Memory ("ROM"), magnetic storage devices, optical storage devices, or any other suitable information storage device or a combination of these devices. Memory 121 may include any suitable information for use in the operation of robot 120. Additionally, memory 121 may be a component external to (or may be partially external to) robot 120. Memory 121 may be located at any location suitable for memory 121 to communicate with robot 120.

Interface 122 of robot 120 represents any suitable computer element that can receive information from network 160, transmit information through network 160, perform suitable processing of the information, communicate to other components (e.g., computer 130) of system 100, or any combination of the preceding. For example, interface 122 of robot 120 may receive action data from robot action determiner module 110 via network 160 (see notation 162 of FIG. 1) and/or transmit feedback pertaining to the received action data to robot action determiner module 110 via network 160 (see notation 164 of FIG. 1). As another example, interface 122 of robot 120 may transmit feedback to computer 130 via network 160 (see notation 166 of FIG. 1) and/or receive action data and/or feedback from computer 130 via network 160. Interface 122 represents any port or connection, real or virtual, including any suitable combination of hardware, firmware, and software, including protocol conversion and data processing capabilities, to communicate through a Local Area Network ("LAN"), Wide Area Network ("WAN"), or other communication system that allows the entity associated with system 100 to exchange information between components of system 100.

Processor 123 of robot 120 controls the operation of robot 120 by processing information received from interface 122 and memory 121 or otherwise accessed by processor 123. Processor 123 communicatively couples to interface 122 and memory 121. Processor 123 includes any hardware and/or software that operates to control and process information. Processor 123 may be a programmable logic device, a microcontroller, a microprocessor, any suitable processing device, or any suitable combination of the preceding. Additionally, processor 123 may be a component external to robot 120. Processor 123 may be located in any location suitable for processor 123 to communicate with robot 120. Processor 123 performs operations of robot 120 such as initiating robot 120 to perform one or more actions associated with action data received from robot action determiner module 110.

Robot sensor 125 may be a device associated with (e.g., attached to or included within) robot 120 that can detect and respond to input (e.g., input from a physical environment such as heat, motion, moisture, light, or pressure). Robot sensor 125 may be, for example, a two-dimensional vision sensor, a three-dimensional vision sensor, a force torque sensor, a collision detection sensor, or a tactile sensor. In certain embodiments, robot sensor 125 detects input, such as motion, and transmits feedback associated with the sensor input (e.g., robot sensor data) to one or more components of system 100 (e.g., robot action determiner 110 and/or computer 130). Robot sensor 125 may be one robot sensor in a collection of robot sensors 125[a-n]. Each such robot sensor (illustrated here as 125[a] . . . 125[n]) is one among a total of N, where N is any suitable integer. In certain embodiments, robot sensors 125a-n include more than one type of sensor (e.g., a motion sensor and a temperature sensor).

Computer 130 of system 100 may be any computing device that provides a mechanism to view and interact with information received from one or more components (e.g., robot action determiner module 110) of system 100. In certain embodiments, computer 130 includes a graphical user interface (GUI) that can display information. Computer 130 may display and or highlight, via a GUI, a repair site (e.g., an artery or a wire) located by robot 120. In some embodiments, computer 130 includes a VR/AR display. The VR/AR display of system 100 may cross-reference and visually overlay observations from other historical procedures, such as video references, schematic diagrams, and/or diagnostic diagrams. Computer 130 may also display details from observed non-visual conditions such as sonar, thermal, or density values. For example, computer 130 may receive thermal data from robot sensor 125 (e.g., a temperature sensor) and display the temperature associated with the thermal data on a display.

Computer 130 may be located on the physical premises of the entity associated with system 100 (e.g., one or more buildings at one or more geographical locations of the entity). For example, for an entity such as a healthcare provider, computer 130 may be located within a hospital of the healthcare provider. In some embodiments, computer 130 is located outside of the physical premises of the entity associated with system 100 (e.g., at a residence of operator 132). For security purposes, operator 132 of computer 130 may connect to network 160 of the entity associated with system 100 via a virtual private network (VPN).

Computer 130 includes an interface that can receive information from network 160, transmit information through network 160, perform suitable processing of the information, communicate to other components (e.g., robot action determiner module 110) of system 100, or any combination of the preceding. For example, an interface of computer 130 may receive feedback from robot 120 via network 160 (see notation 166 of FIG. 1) and/or transmit feedback to robot action determiner module 110 via network 160 (see notation 168 of FIG. 1). In certain embodiments, computer 130 and robot action determiner module 110 may be integrated into a single component. For example, robot action determiner module 110 may be an application run by computer 130.

Operator 132 may be any person interacting with computer 130 of system 100 (e.g., a technician, a surgeon, or a surgeon's assistant) who is involved with overseeing the determination and evaluation of action data representing an action to be performed by robot 120. For example, operator 132 may be responsible for viewing one or more images received from robot 120 or robot action determiner 110 on computer 130. In certain embodiments, operator 132 analyzes action data received from robot action determiner module. For example, operator 132 may interact with a display (e.g., a GUI and/or a VR/AR display) of computer 130 by viewing an image of a repair site location discovered by robot 120 on the display of computer 130 and highlighting a particular location (e.g., an artery or a wire) for repair by selecting (e.g., touching) the particular location within the image. In certain embodiments, operator 132 of computer 130 verifies action data to be performed by robot 120. Operator 132 may send a verification to robot action determiner module 110 to transmit the action data to robot 120. In some embodiments, operator 132 alters the action data received from robot action determiner module 110 and sends the altered action data to robot action determiner module 110 for transmission to robot 120.

Operator 132 may use computer 130 to connect to robot action determiner module 110 and/or robot 120 over network 160. In certain embodiments, operator 132 of computer 130 is authorized by the entity associated with system 100 to access robot action determiner 110 and/or robot 120. In some embodiments, operator 132 accesses robot action determiner 110 by logging into a home page of robot action determiner 110 via computer 130. Operator 132 may be requested to enter an identification associated with the entity associated with system 100 to access robot action determiner module 110 via a web portal.

Although this disclosure described particular operations being performed by an operator 132 of computer 130, the present disclosure contemplates any suitable component performing these features. For example, in addition or as an alternative to operator 132 of computer 130 performing these operations, the present disclosure contemplates a software application automatically performing these operations. As a particular example, the software application may automatically verify action data to be performed by robot 120 and send a verification to robot action determiner module 110.

User sensor 140 may be a device associated with (e.g., attached to) user 150 that can detect and respond to input (e.g., input from a physical environment such as heat, motion, moisture, light, or pressure). User sensor 150 may be, for example, a motion sensor. In some embodiments, user sensor 140 is worn by user 150. For example, user sensor 140 may be integrated into a glove, an elbow pad, a knee pad, or eyewear worn by user 150. In some embodiments, user sensor 140 may be associated with an object. For example, user sensor 140 may be attached to a physical instrument (e.g., a surgical knife or a screwdriver). In certain embodiments, user sensor 140 detects input, such as a gesture, and transmits data representing the input (e.g., user sensor data) to one or more components of system 100 (e.g., robot action determiner 110 and/or computer 130). For example, user sensor 140 may transmit user sensor data to robot action determiner 110 via network 160 (see notation 170 of FIG. 1). User sensor 140 may be one user sensor in a collection of user sensors 140[*a-n*]. Each such user sensor (illustrated here as 140[*a*] . . . 140[*n*]) is one among a total of N, where N is any suitable integer. In certain embodiments, user sensors 140*a-n* include more than one type of sensor (e.g., a motion sensor and a temperature sensor).

User 150 of system 100 may be any person or thing associated with system 100 (e.g., a technician, a surgeon, or a machine) that is capable of performing one or more gestures. A gesture may be any movement of a part of a body of user 150. For example, a gesture may be a jab, an uppercut, a throw, a lift, a block, a sway, a blink, and/or a kick. In certain embodiments, a gesture may be a combination of movements, such as a wave and a finger movement. In some embodiments, a gesture of user 150 is multi-modal. For example, a gesture may involve speech and eye movement. In the illustrated embodiment, user 150 is associated with (e.g., wearing) user sensor(s) 140. In some embodiments, user 150 makes a gesture while holding a physical object with sensor(s) 140 attached to the physical object. In certain embodiments, user 150 of system 100 is operator 132 of computer 130. For example, user 150 of system 100 and operator 132 of computer 130 of system 100 may both be the same surgeon.

Network 160 of system 100 may include any device or collection of devices that facilitate communication between components of system 100. For example, network 160 may facilitate the transfer of information between robot action determiner module 110, robot 120, computer 130, and user sensor(s) 140. Network 160 can be implemented using any suitable network or networking technology. For example, one or more portions of network 160 may include an ad hoc network, an intranet, an extranet, a VPN, LAN, a wireless LAN (WLAN), a WAN, a wireless WAN (WWAN), a metropolitan area network (MAN), a portion of the Internet, a portion of the Public Switched Telephone Network (STN), a cellular telephone network, or a combination of two or more of these.

In certain embodiments, network 160 is a private network that isolates users and workgroups external to the entity. As an example, network 160 may only be accessible to an operator 132 on the premises of the entity associated with system 100. As another example, network 160 may be accessible to users 122 via a secure link (e.g., a VPN). The VPN may allow operator 132 of computer 130 to send and receive data as if computer 130 were directly connected to network 160 while maintaining the security of network 160.

In certain embodiments, network 160 facilitates communication between one or more components of system 100 (e.g., robot action determiner module 110) hosted in a cloud environment.

System 100 illustrates just one example of a system for determining and evaluating data representing an action to be performed by a robot (e.g., robot 120). Modifications, additions, or omissions may be made to system 100. For example, system 100 may include any number of robot action determiner modules 110. As another example, system 100 may include any number of robots 120. As still another example, system 100 may coordinate actions of multiple robots 120 by mapping action data for each robot 120 to the same gesture of user 150. Furthermore, the components of system 100 may be integrated or separated. For example, robot action determiner module 110 and computer 130 may be incorporated into a single component.

In operation of an example embodiment of system 100, robot action determiner module 110 receives sensor input data representing a gesture (e.g., a jab) from user sensor(s) 140 attached to user 150. Robot action determiner module 110 determines, based on the sensor input data representing the gesture, action data representing an action to be performed by robot 120 (e.g., cracking a patient's rib). Robot action determiner module 110 then evaluates the action data representing the action to be performed by robot 120 in light of evaluation data (e.g., historical data pertaining to past similar surgeries) and determines to transmit the action data to robot 120 based on a comparison of the action data and the evaluation data. Robot action determiner module 110 initiates transmission (see notation 168) of the action data, the evaluation data, and a request to approve the action data for transmission to robot 120 to computer 130 and accesses a confirmation from computer 130 to transmit the action data to robot 130. Based on this confirmation, robot action determiner module 110 initiates transmission of the action data to robot 120 via network 160 (see notation 162).

In operation of an example embodiment of system 100, robot action determiner module 110 accesses feedback from robot 120 (e.g., a notification that a first action has been completed) based at least in part on robot 120 performing the first action (e.g., cracking the patient's rib). Robot action determiner module 110 determines, based on the feedback from robot 120, action data representing a second action to be performed by robot 120. Robot action determiner module 110 evaluates the action data representing the second action to be performed by robot 120 in light of evaluation data. Robot action determiner module 110 determines, based on the evaluation data, not to transmit the action data representing the second action to be performed by robot 120 to robot 120. Robot action determiner module 110 alters the action data in light of evaluation data and initiates transmission (see notation 168) of the altered action data to operator 132 of computer 130. Robot action determiner module 110 determines that operator 132 verified the altered action data for transmission to robot 120 and initiates transmission of the altered action data to robot 120 (see notation 162).

In operation of an example embodiment of system 100, robot action determiner module 110 accesses user sensor data (e.g., data representing a jabbing gesture performed by user 150) from user sensor(s) 140. Robot action determiner module 110 determines, based on the user sensor data, action data representing an action (e.g., a movement) to be performed by robot 120. Robot action determiner module evaluates the action data representing the action to be performed by robot 120 in light of evaluation data. Robot action determiner module 110 initiates transmission (see notation 168) of the action data to operator 132 of computer 130. Robot action determiner module 110 accesses feedback from operator 132. Robot action determiner module 110 determines that the feedback from operator 132 proposes an alteration to the action data. Robot action determiner module 110 alters the action data in accordance with the feedback from operator 132 and initiates transmission of the altered action data to robot 120 (see notation 162).

Figure 2:
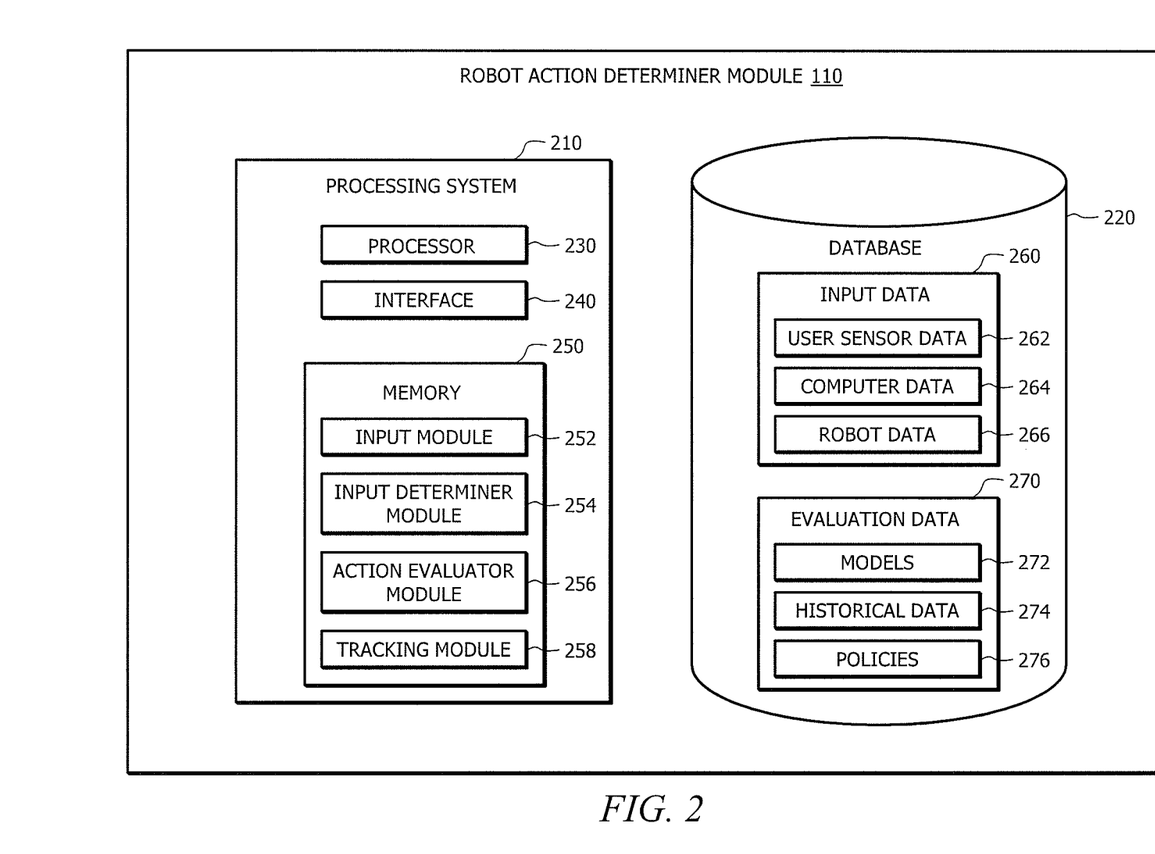
FIG. 2 illustrates details of an example of a robot action determiner module used in the system of FIG. 1, according to certain embodiments.

FIG. 2 illustrates details of an example of a robot action determiner module 110 used in the system of FIG. 1, according to certain embodiments. In certain embodiments, robot action determiner module 110 evaluates action data representing an action to be performed by robot 120 in light of evaluation data. In the illustrated embodiment, robot action determiner module 110 includes a processing system 210 and a database 220. The elements of robot action determiner module 110 may be implemented using any suitable combination of hardware, firmware, and software.

Robot action determiner module 110 may be implemented using one or more computer systems at one or more locations. Each computer system may include any appropriate input devices, output devices, mass storage media, processors, memory, or other suitable components for receiving, processing, storing, and communicating data. For example, each computer system may include a personal computer, workstation, network computer, kiosk, wireless data port, PDA, one or more IP telephones, one or more servers, a server pool, switch, router, one or more processors within these or other devices, or any other suitable processing device. Robot action determiner module 110 may be a stand-alone computer or may be a part of a larger network of computers associated with an entity. In certain embodiments, robot action determiner module 110 is a program. For example, robot action determiner module 110 may be an application downloaded on computer 130 of FIG. 1. In some embodiments, robot action determiner module 110 is hosted in a cloud environment.

Processing system 210 of robot action determiner module 110 determines and evaluates data received from robot 120, computer 130, user sensors 140 of user 150, and or data stored in database 220. Processing system 210 includes a processor 230, an interface 240, and a memory 250. Memory 250 of processing system 210 includes an input module 252, an input determiner module 254, an action evaluator module 256, and a tracking module 258.

Processor 230 of robot action determiner module 110 controls the operation of robot action determiner module 110 by processing information received from interface 240 and memory 250 or otherwise accessed by processor 230. Processor 230 communicatively couples to interface 240 and memory 250. Processor 230 includes any hardware and/or software that operates to control and process information. For example, processor 230 controls the operation of input module 252, input determiner module 254, action evaluator module 256, and tracking module 258. Processor 230 may be a programmable logic device, a microcontroller, a microprocessor, any suitable processing device, or any suitable combination of the preceding. Additionally, processor 230 may be a component external to robot action determiner module 110. Processor 230 may be located in any location suitable for processor 230 to communicate with robot action determiner module 110. Processor 230 performs operations of robot action determiner module 110 such as determining and evaluating data representing an action to be performed by robot 120.

Interface 240 of robot action determiner module 110 represents any suitable computer element that can receive information from network 160, transmit information through network 160, perform suitable processing of the information, communicate to other components (e.g., computer 130) of system 100, or any combination of the preceding. For example, interface 240 may receive data from user sensor(s) 140, transmit data (e.g., action data) to robot 120, transmit data to computer 130, and receive data from computer 130. Interface 240 represents any port or connection, real or virtual, including any suitable combination of hardware, firmware, and software, including protocol conversion and data processing capabilities, to communicate through a Local Area Network ("LAN"), Wide Area Network ("WAN"), or other communication system that allows the entity associated with system 100 to exchange information between components of system 100.

Memory 250 of robot action determiner module 110 stores, permanently and/or temporarily, received and transmitted information, as well as system software, control software, and other software for robot action determiner module 110, and a variety of other information. Memory 250 may store information for execution by processor 230. In the illustrated embodiment, memory 250 stores the following applications of robot action determiner module 110: input module 252, input determiner module 254, action evaluator module 256, and tracking module 258. Memory 250 of robot action determiner module 110 may store data received from robot 120, robot sensor(s) 125, computer 130, user sensor(s) 140, and/or database 220.

Memory 250 includes any one or a combination of volatile or non-volatile local or remote devices suitable for storing information. For example, memory 250 may include Random Access Memory ("RAM"), Read-only Memory ("ROM"), magnetic storage devices, optical storage devices, or any other suitable information storage device or a combination of these devices. Memory 250 may include any suitable information for use in the operation of robot action determiner module 110. Additionally, memory 250 may be a component external to (or may be partially external to) robot action determiner module 110. Memory 250 may be located at any location suitable for memory 250 to communicate with robot action determiner module 110.

Input module 252 of processing system 210 may access data received from robot 120, robot sensor(s) 125, computer 130, user sensor(s) 140, and or database 220. For example, input module 252 may access data received via interface 240 of processing system 210 from user sensor(s) 140. In certain embodiments, the accessed data may represent one or more gestures (e.g., a jabbing gesture performed by user 150). Input module 252 of processing system 210 may transmit data to robot 120, robot sensor(s) 125, computer 130, and/or database 220. For example, input module 240 may transmit accessed user sensor data to memory 250 or database 220 for storage. As another example, input module 252 of processing system 210 may transmit data to interface 240 for transmission to robot 120. In certain embodiments, input module 252 transmits data to input determiner module 254 of processing system 210.

In the illustrated embodiment, input determiner module 254 of processing system 210 receives data (e.g., user sensor data) from input module 252 and determines, based on the received data, action data representing an action to be performed by robot 120. In certain embodiments, action data representing an action to be performed by robot 120 may include data stored in memory 250 and/or database 220. In some embodiments, action data is data representing one or more movements to be performed by robot 120. Action data may instruct robot 120 to perform one or more movements of one or more parts of robot 120. For example, action data may instruct robot 120 to move an arm of robot 120 a certain distance (e.g., one millimeter) in a certain direction. In certain embodiments, action data may instruct robot 120 to perform one or more measurements. For example, action data may instruct robot 120 to measure temperature, humidity, or pressure. In some embodiments, database 220 may store action data representing a pre-defined set of actions (e.g., movements) to be performed by robot 120.

Data received by input determiner module 254 may represent a gesture, such as a jab, performed by user 150, and input determiner module 110 may determine action data representing an action to be performed by robot 120, such as breaking a rib of a patient, by mapping the received data representing the jab to the action data representing breaking a rib. In certain embodiments, the received data may represent a gesture, such as a circle or sweep of a wrist of user 150, and input determiner module 254 may determine action data representing an action to be performed by robot 120, such as initiating an operation, by mapping the input data representing the circle or sweep of the wrist to the action data representing robot 120 initiating the operation.

In certain embodiments, input determiner module 254 associates data received from input module 252 with one or more profiles of a particular user. For example, input module 252 may receive user sensor data representing a gesture (e.g., a jabbing gesture) performed by User A, and input determiner module 254 may associate the user sensor data with a profile of User A. In certain embodiments, input determiner module 254 determines action data representing an action to be performed by robot 120 based at least in part on the user profile associated with the data received from input module 252. For example, robot action determiner module 110 may store different instructions (e.g., instructions for cutting an artery) in memory 250 for different users, and input determiner module 254 may determine action data representing an action to be performed by robot 120 (e.g., the action of cutting an artery) by mapping user sensor data representing a gesture performed by User X (e.g., a slicing gesture) to a set of instructions specific to User X (e.g., User X's instructions for cutting an artery). In certain embodiments, input determiner module 254 transmits the action data to action evaluator module 256.

Action evaluator module 256 of robot action determiner module 110 receives action data representing the action to be performed by robot 120 from input determiner module 254 and evaluates the action data in light of evaluation data. Evaluation data may be data used to determine whether to transmit the action data representing the action to be performed by robot 120. For example, action evaluator module 256 may determine to transmit the action data representing the action to be performed by robot 120 to robot 120. As another example, action evaluator module 256 may determine to transmit the action data representing the action to be performed by robot 120 to computer 130. In certain embodiments, action evaluator module 256 may determine to alter the action data representing the action to be performed by robot 120.

In certain embodiments, action evaluator module 256 accesses feedback from robot 120. For example, input module 252 may access feedback from sensor(s) 125 of robot 120 via interface 240 and transmit the feedback to action evaluator module 256. The feedback may be based on robot 120 performing one or more actions (e.g., the action associated with the action data). For example, action evaluator module 256 may transmit action data to robot 120 via interface 240 instructing robot 120 to break a patient's rib, and action evaluator module 256 may access feedback resulting from robot 120 breaking the patient's rib, such as feedback representing completion of the task. In certain embodiments, the feedback may include one or more positions of sensor(s) 125 attached to or included within robot 120. For example, the feedback may include Global Positioning System (GPS) data of sensor 125a attached to robot 120. In some embodiments, the feedback may include one or more conditions observed by robot 120. For example, robot 120 may perform the action of breaking a patient's rib, and the feedback may include resistance data resulting from the pressure applied by robot 120 to break the patient's rib. As another example, the feedback may include an image taken by robot 120 (e.g., an image of a broken rib or an image of a located artery). As still another example, the feedback may include data associated with environmental conditions (e.g., temperature, humidity, barometric pressure, and/or air flow).

In certain embodiments, action evaluator module 256 accesses feedback from computer 130. For example, input module 252 may access feedback from computer 130 via interface 240. The feedback may be based on input from operator 132 into computer 130. For example, action evaluator module 256 may transmit action data representing an action (e.g., the action of breaking a patient's rib) to computer 130, and action evaluator module 256 may access feedback from operator 132 cancelling the action. As another example, action evaluator module 256 may transmit action data representing an action (e.g., the action of sewing six stitches in a patient) to computer 130, and action evaluator module 256 may access feedback from operator 132 altering the action data to represent a different action (e.g., the action of sewing eight stitches in the patient).

In certain embodiments, action evaluator module 256 determines to alter action data representing the action to be performed by robot 120 based on evaluating the action data in light of the evaluation data. For example, action data may include data instructing robot 120 to make a six-inch incision down a breastbone of a patient during open-heart surgery, and action evaluator module 256 may alter the incision length to three inches based on evaluation data showing historical incisions of three inches during open-heart surgery. In certain embodiments, action evaluator module 256 may transmit the altered action data to computer 130. In certain embodiments, action evaluator module 256 may access a verification of the altered action data from computer 130 prior to transmitting the altered action data to robot 120. In some embodiments, action evaluator module 256 may transmit the altered action data to robot 120 without prior verification from computer 130.

Tracking module 258 of robot action determiner module 110 may track and/or record information from current and/or past activities. In certain embodiments, the tracked information is stored in robot action determiner module 110. For example, the tracked information may be stored as evaluation data in memory 250 or a database of robot action determiner module 110. Tracking module 258 may track and record data in real time as it occurs during a procedure, such as open heart surgery, and transmit the recorded data to computer 130 for feedback from operator 132. Tracking module 258 may track and record data from historical operations to be used by robot action determiner module 110 as evaluation data. In certain embodiments, tracking module 258 tracks and/or records feedback from operator 132 and/or robot 120. In some embodiments, tracking module 258 synchronizes the tracked or recorded data to action data (e.g., a task list compiled for an operation). In certain embodiments, tracking module 258 may notify operator 132 of any deviations and anomalies of the action data as compared to the tracked and recorded data.

Database 220 of robot action determiner module 110 may be any one or a combination of volatile or non-volatile local or remote devices suitable for storing information. For example, database 220 may include Random Access Memory ("RAM"), Read-only Memory ("ROM"), magnetic storage devices, optical storage devices, or any other suitable information storage device or a combination of these devices. Database 220 may include any suitable information for use in the operation of robot action determiner module 110. Additionally, database 220 may be a component external to (or may be partially external to) robot action determiner module 110. Database 220 may be located at any location suitable for database 220 to communicate with robot action determiner module 110. In certain embodiments, database 220 may be hosted in a cloud environment.

Database 220 may store input data 260 and evaluation data 270. Input data 260 includes user sensor data 262, computer data 264, and robot data 266. User sensor data 262 of input data 260 is data received from user sensor(s) 140 associated with (e.g., worn by) user 150. For example, user sensor data 262 may be input data 260 representing one or more gestures (e.g., a jab, an uppercut, a throw, a lift, a block, a sway, a kick, or a finger count) of user 150.

Computer data 264 of input data 260 may be data received from computer 130. For example, input module 252 of processing system 210 may receive computer data 264 from computer 130 and transmit computer data 264 to database 220. In certain embodiments, computer data 264 includes action data representing one or more actions to be performed by robot 120. In some embodiments, computer data includes altered action data resulting from operator 132 viewing and modifying the action data received from action evaluator module 256. In certain embodiments, computer data includes a verification of action data. For example, operator 132 of computer 130 may view action data, confirm that the action data should be transmitted to robot 120, and transmit a verification or instruction to input determiner module 254 to transmit the action data to robot 120. Input module 252 may then transmit this verification or instruction to database 220 for storage. In certain embodiments, computer data 264 includes data input into computer 130 by operator 132 of system 100. In some embodiments, computer data 264 includes data automatically transmitted from computer 130 to robot action determiner module 110 without input from operator 132.

Robot data 266 of input data 260 may be data received from robot 120. In certain embodiments, robot data 266 is data received from robot sensor(s) 125 associated with (e.g., attached to) or included within with robot 120. For example, robot data 266 may include data received from a two-dimensional vision sensor, a three-dimensional vision sensor, a force torque sensor, a collision detection sensor, or a tactile sensor. In certain embodiments, robot data 266 is feedback received from robot 120 as a result of robot 120 performing one or more actions associated with action data. For example, robot data 266 may include a GPS location of robot 120 after robot 120 performs a movement. As another example, robot data 266 may include a notification that robot 120 has completed the action data.

Evaluation data 270 of database 220 may be any data used by action evaluator module 256 of processing system 210 to evaluate action data received from input determiner module 254 of processing system 210. In certain embodiments, evaluation data 270 is data that assists action evaluator module 256 in learning what action a machine (e.g., robot 120) should perform. Robot action determiner module 110 may study evaluation data 270 to make predictions (e.g., predictions for action data) based on, for example, pattern recognition. Evaluation data 270 may assist action evaluator module 256 in detecting anomalies in the action data (e.g., a deviation from a standard). In some embodiments, evaluation data 270 may assist action evaluator module 256 in detecting anomalies in an environment (e.g., a patient with an abnormal condition). In certain embodiments, evaluation data 270 is used to predict one or more actions. Evaluation data 270 may be used to verify that the action data is in agreement with a predicted action.

Evaluation data may include model(s) 272, historical data 274, and one or more policies 276. Model 272 is data that includes example instructions for performing one or more actions. For example, model 272 may be may be a procedural model with example instructions for cutting an artery in a patient. As another example, model 272 may be example instructions for moving a patient's heart. In certain embodiments, model 272 may be used by input determiner module 254 to determine action data. For example, input determiner module 254 may map user sensor data to model 272. In certain embodiments, model 272 is learned by system 100. For example, robot action determiner module 110 may create model 272 by learning to execute an action based on sensory feedback.

Historical data 274 of evaluation data 270 may be data based on one or more historical observations. In certain embodiments, historical data 274 includes data from a previous procedure. For example, historical data 274 may include action data from a previous open heart surgery. In some embodiments, historical data 274 may include problems recorded during a previous procedure. For example, historical data 274 may include data indicating that an infection resulted from performing a certain procedure in accordance with particular action data. In certain embodiments, historical data may include environmental conditions during past procedures. For example, historical data 274 may include data indicating that the average chest incision length during past open heart surgeries was six inches. As another example, historical data 274 may include data indicating that the average temperature of the operating room during open heart surgery was 67 degrees Fahrenheit.

Policies 274 of evaluation data 270 may be data including one or more rules applicable to certain activities. In certain embodiments, policies 274 include standards set forth by an entity. For example, policy 274 may be a standard that the operating room temperature must be between 65 and 70 degrees Fahrenheit during each medical procedure. In some embodiments, policies 274 include rules set forth by operator 132 of computer 130. For example, operator 132 may set a policy 274 that all chest incisions for open heart surgery must be between three and six inches.

Evaluation data 270 may be data collected while an activity (e.g., a repair) is taking place. In certain embodiments, evaluation data 270 is an observable condition of an object (e.g., a patient or a wire) that is the subject of robot 120. For example, evaluation data 270 may be a vital sign of a patient that is a subject of robot 120, such as a patient's temperature or heart rate. In some embodiments, evaluation data 270 may be an environmental condition surrounding robot 120, such as a temperature or humidity of an operating room. In certain embodiments, evaluation data 270 is data learned by one or more components of system 100. For example, robot action determiner module 110 may learn, from pattern recognition, that user sensor data 262 from user sensor(s) 140, such as data representing an uppercut gesture, is associated with a particular user, such as Surgeon A, based on a certain configuration of Surgeon A's hand (e.g., an open rather than closed fist).

Modifications, additions, or omissions may be made to robot action determiner module 100 of FIG. 2. For example, robot action determiner module 100 may include any number of databases 220. Furthermore, the components of robot action determiner module 100 may be integrated or separated. For example, input determiner module 254 and action determiner module 256 may be incorporated into a single component.

Figure 3:
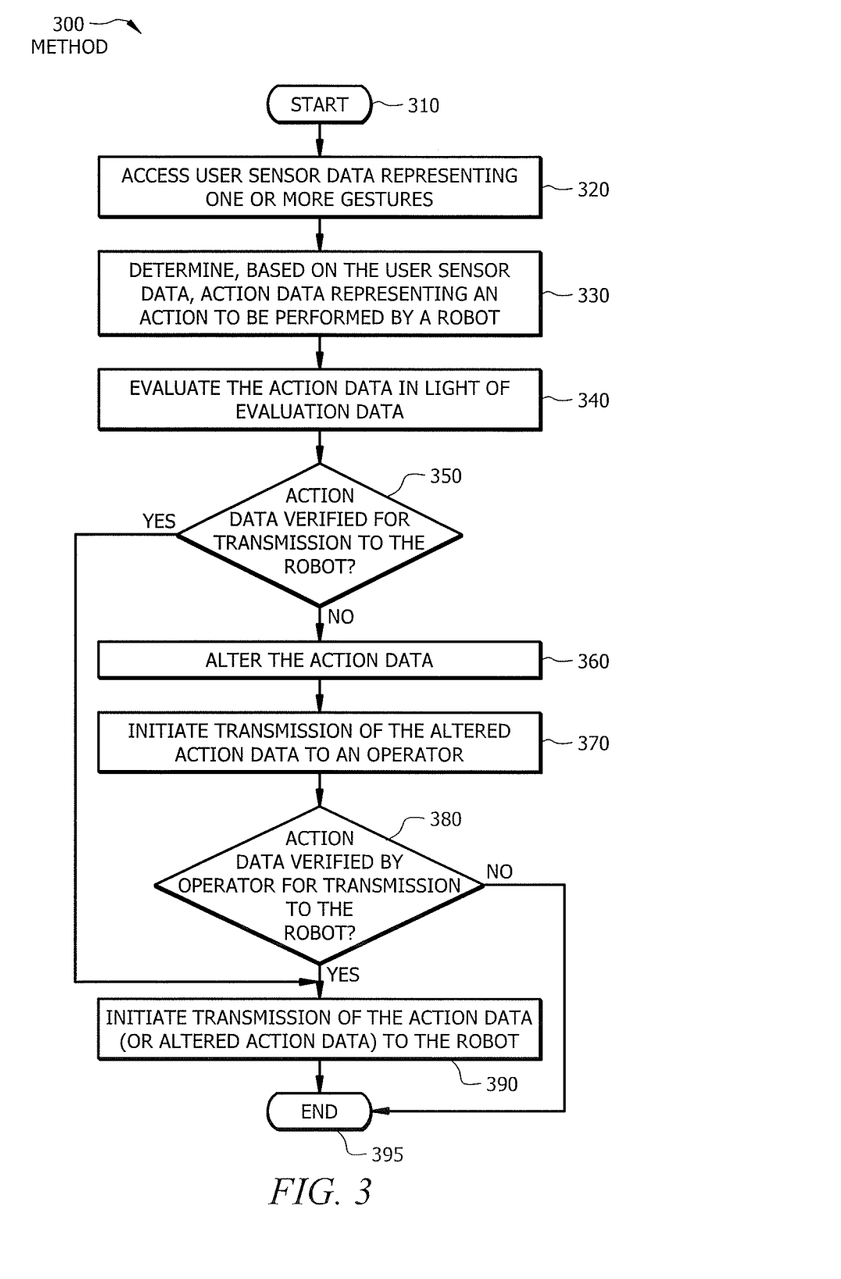
FIG. 3 illustrates an example of a method for determining and evaluating data representing an action to be performed by a robot, according to certain embodiments.

FIG. 3 illustrates an example of a method 300 for determining and evaluating data representing an action to be performed by robot 120, according to certain embodiments. The method begins at step 310. At step 320, processor 230 of robot action determiner module 110 accesses user sensor data 262 from user sensor(s) 140. In certain embodiments, user sensor data 262 represents one or more gestures performed by user 150. For example, user sensor data 262 may represent a jabbing gesture performed by user 150. Method 300 may then proceed to step 330.

At step 330, processor 230 of robot action determiner module 110 determines, based on user sensor data 262, action data representing an action to be performed by robot 120. For example, processor 230 may map user sensor data 262 to the action data by associating the one or more gestures performed by user 150 with one or more movements to be performed by robot 120. In certain embodiments, the action data represents a pre-defined set of movements to be performed by robot 120. Method 300 may then proceed to step 340.

At step 340, processor 230 of robot action determiner module 110 evaluates the action data representing the action to be performed by robot 120 in light of evaluation data 270. In certain embodiments, evaluation data 270 includes one or more models 272, historical data 274, and/or one or more policies 276. Processor 230 may evaluate the action data to be performed by robot 120 by comparing the action data to evaluation data 270. For example, the action data may instruct robot 120 to cut a three-inch incision in a patient's chest for bypass surgery, and processor 230 may compare this action data to historical data 274 from past surgeries that instructed robot 120 to cut a six-inch incision in a patient's chest for bypass surgery. Method 300 may then proceed to step 350.

At step 350, processor 230 of robot action determiner module 110 determines whether to transmit the action data to be performed by robot 120 to robot 120. In certain embodiments, processor 230 verifies that the action data should be transmitted to robot 120. For example, the action data may instruct robot 120 to cut a three-inch incision, and the evaluation of the action data may confirm that a three-inch incision was commonly performed in past similar procedures. If processor 230 verifies that the action data should be transmitted to robot 120, method 300 proceeds to step 390, and processor 230 initiates transmission of the action data to robot 120. Otherwise, method 300 proceeds to step 360.

At step 360, processor 230 of robot action determiner module 110 alters the action data. In certain embodiments, processor 230 alters the action data in light of evaluation data 270. For example, processor 230 may alter action data instructing robot 120 to cut a three-inch incision in a patient's chest for bypass surgery to instruct robot 120 to cut a six-inch incision in the patient's chest to match historical data 274 from past similar surgeries. Method 300 may then move to step 370.

At step 370, processor 230 of robot action determiner module 110 initiates transmission of the altered action data to operator 132 of computer 130. Operator 132 may view the altered action data on a display of computer 130. For example, operator 132 may view an image of highlighted artery amongst several arteries via a GUI of computer 130. In certain embodiments, operator 132 may listen to a verbal interpretation of the altered action data rather than or in addition to viewing the altered action data on a display of computer 130.

At step 380, processor 230 of robot action determiner module 110 determines whether operator 132 has verified the action data for transmission to robot 120. For example, processor 230 may determine that operator 132 verified the action data for transmission to robot 120 by accessing a selection made by operator 132 on computer 130 (e.g., a selection of a highlighted artery displayed on computer 130). As another example, processor 230 may verify that operator 132 verified the action data for transmission to robot 120 by accessing a verbal command (e.g., "yes") of operator 132. If processor 230 of robot action determiner module 110 determines that operator 132 verified the action data for transmission to robot 120, method 300 proceeds to step 390. Otherwise, method 300 proceeds to step 395, where method 300 ends.

At step 390, processor 230 of robot action determiner module 110 initiates transmission of the altered action data to robot 120. Method 300 may then proceed to step 395, where method 300 ends.

Modifications, additions, or omissions may be made to method 300 depicted in FIG. 3. Method 300 may include more, fewer, or other steps. For example, at step 360, rather than altering the action data, processor 230 may initiate transmission of the action data to operator 230. As another example, at step 370, processor 230 may initiate transmission of several options for altered action data to operator 132, and at step 380, operator 132 may verify one option of the several options for altered action data for transmission to robot 120. Steps may also be performed in parallel or in any suitable order. While the present disclosure describes particular components as performing particular steps of method 300, the present disclosure contemplates any suitable component of system 100 performing any step of method 300.

Figure 4:
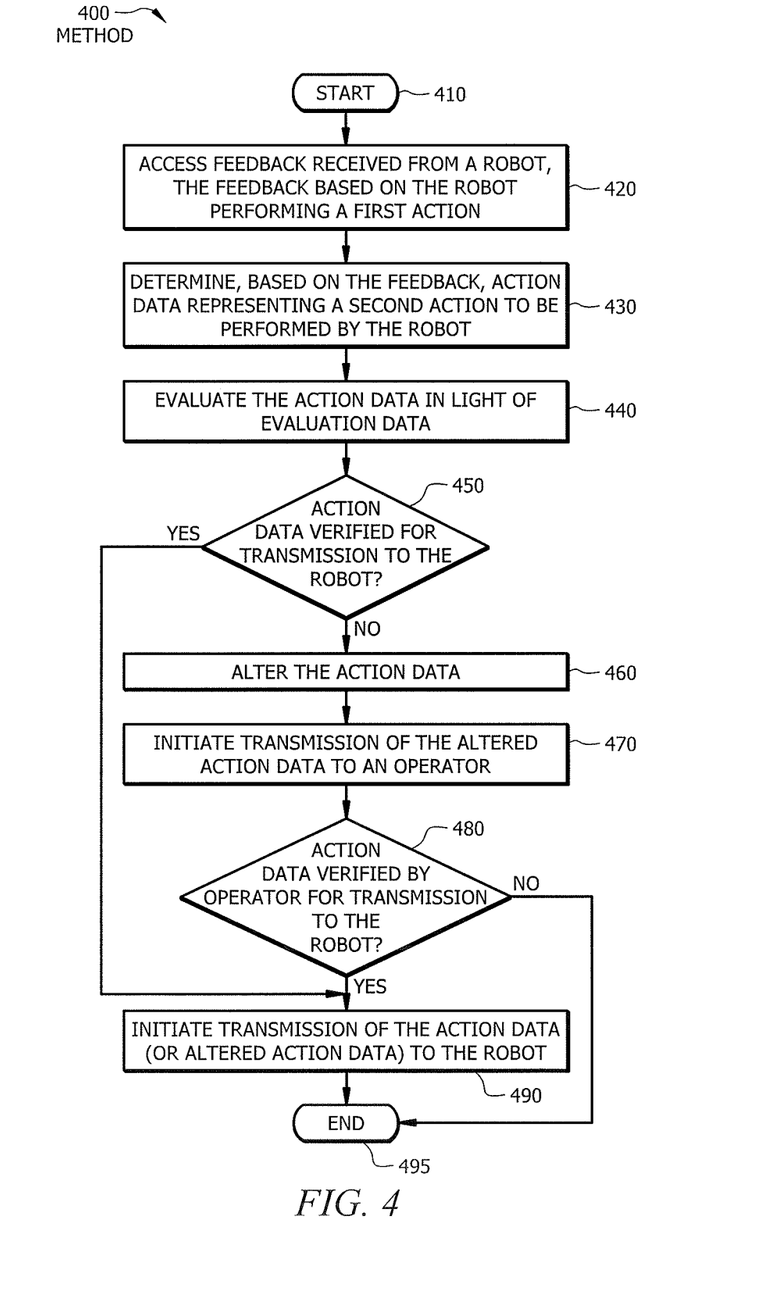
FIG. 4 illustrates an example of a method for determining and evaluating data representing an action to be performed by a robot, according to certain embodiments.

FIG. 4 illustrates an example of a method 400 for determining and evaluating data representing an action to be performed by a robot, according to certain embodiments. The method begins at step 410. At step 420, processor 230 of robot action determiner module 110 accesses feedback from robot 120. The feedback may be any information associated with robot 120, such as data pertaining to robot 120 performing one or more actions or data associated with environmental conditions surrounding robot 120. In certain embodiments, the feedback is based on robot 120 performing a first action. In some embodiments, the feedback may be feedback received from robot sensor(s) 125 (e.g., a temperature reading or GPS coordinates).

In certain embodiments, the first action may be associated with the action data of method 300. For example, the action data of method 300 may represent a first action of stitching up a wound with ten stitches to be performed by robot 120, and upon transmission of the action data to robot 120 at step 390 of method 300, robot may perform the first action of sewing the ten stitches. Processor 230 of robot action determiner module 110 may then access feedback based on robot 120 sewing ten stitches. The feedback may include a confirmation that robot has completed sewing ten stitches, yet blood is still exiting the wound.

In certain embodiments, processor 230 of robot action determiner module 110 accesses feedback based on robot 120 performing a first action before robot 120 completes the first action. For example, the first action may be stitching up a wound with ten stitches, and processor 230 may access feedback based on robot 120 performing just the first stitch. In certain embodiments, processor 230 accesses feedback in real time. For example, processor 230 may continuously access feedback as robot 120 stitches up the wound, providing feedback after every stitch. This real-time feedback allows robot action determiner module 110 to take corrective measures as the procedure progresses. For example, the feedback received from robot 120 after robot 120 completes seven stitches may indicate that the wound is closed. Method 400 may then proceed to step 430.

At step 430, processor 230 of robot action determiner module 110 determines, based on the feedback from robot 120, action data representing a second action to be performed by robot 120. In certain embodiments, the feedback is based on robot performing the first action. For example, processor 230 may receive feedback indicating that robot 120 performed a first action of stitching up a wound with ten stitches, yet blood is still exiting a wound. Based on this feedback, processor 230 may determine action data representing a second action of sewing three additional stitches to close up the wound. In certain embodiments, the action data represents a pre-defined set of movements to be performed by robot 120. For example, the action data may represent a second action of sewing three stitches and then exiting the repair site. Method 400 may then proceed to step 440.

At step 440, processor 230 of robot action determiner module 110 evaluates the action data representing the second action to be performed by robot 120 in light of evaluation data 270. In certain embodiments, evaluation data 270 includes one or more models 272, historical data 274, or one or more policies 276. Processor 230 may evaluate the action data to be performed by robot 120 by comparing the action data to evaluation data 270. For example, the action data may instruct robot 120 to sew stitches one millimeter apart to complete closure of a gushing wound, and processor 230 may compare this action data to historical data 274 from past surgeries that instructed robot 120 to sew stitches two millimeters apart.

At step 450, processor 230 of robot action determiner module 110 determines whether to transmit the action data to be performed by robot 120 to robot 120. In certain embodiments, processor 230 verifies that the action data should be transmitted to robot 120. For example, the action data may instruct robot 120 to sew stitches one millimeter apart, and the evaluation of the action data may confirm that sewing stitches one millimeter apart was commonly performed in past similar procedures. If processor 230 verifies that the action data should be transmitted to robot 120, method 300 may proceed to step 490, and processor 230 initiates transmission of the action data to robot 120. Otherwise, method 400 may proceed to step 460.

At step 460, processor 230 of robot action determiner module 110 alters the action data. In certain embodiments, processor 230 alters the action data in light of evaluation data 270. For example, processor 230 may alter action data instructing robot 120 to sew stitches one millimeter apart to instruct robot 120 to sew stitches two millimeters apart to match historical data 274 from past similar surgeries. Method 300 may then move to step 470.

At step 470, processor 230 of robot action determiner module 110 initiates transmission of the altered action data to operator 132 of computer 130. Operator 132 may view the altered action data on a display of computer 130. For example, operator 132 may view a message on computer 130 stating that action data has been altered to instruct robot 120 to sew stitches two millimeters apart instead of one millimeter apart. As another example, operator 132 may view an overlay of an image representing action data showing stitches at one millimeter apart with an image representing altered action data (e.g., historical data) showing stitches at two millimeters apart. In certain embodiments, operator 132 may listen to a verbal interpretation of the altered action data rather than or in addition to viewing the altered action data on a display of computer 130. For example, operator 132 may hear a verbal message stating the following: "Altering stitch spacing from one millimeter to two millimeters." Method 400 may then proceed to step 480.

At step 480, processor 230 of robot action determiner module 110 determines whether operator 132 verified the altered action data for transmission to robot 120. For example, processor 230 may determine that operator 132 verified the altered action data for transmission to robot 120 by accessing a selection made by operator 132 on computer 130. As another example, processor 230 may verify that operator 132 verified the altered action data for transmission to robot 120 by accessing a verbal command of operator 132. If processor 230 of robot action determiner module 110 determines that operator 132 verified the altered action data for transmission to robot 120, method 400 may proceed to step 490. Otherwise, method 400 may proceed to step 495, where method 400 ends.

At step 490, processor 230 of robot action determiner module 110 initiates transmission of the altered action data to robot 120. Method 400 then proceeds to step 495, where method 400 ends.

Modifications, additions, or omissions may be made to method 400 depicted in FIG. 4. Method 400 may include more, fewer, or other steps. For example, at step 460, rather than altering the action data, processor 230 may initiate transmission of the action data to operator 230. As another example, at step 470, processor 230 may initiate transmission of several options for altered action data to operator 132, and at step 480, operator 132 may verify one option of the several options for altered action data for transmission to robot 120. Steps may also be performed in parallel or in any suitable order. While the present disclosure describes particular components as performing particular steps of method 400, the present disclosure contemplates any suitable component of system 100 performing any step of method 400.

Figure 5:
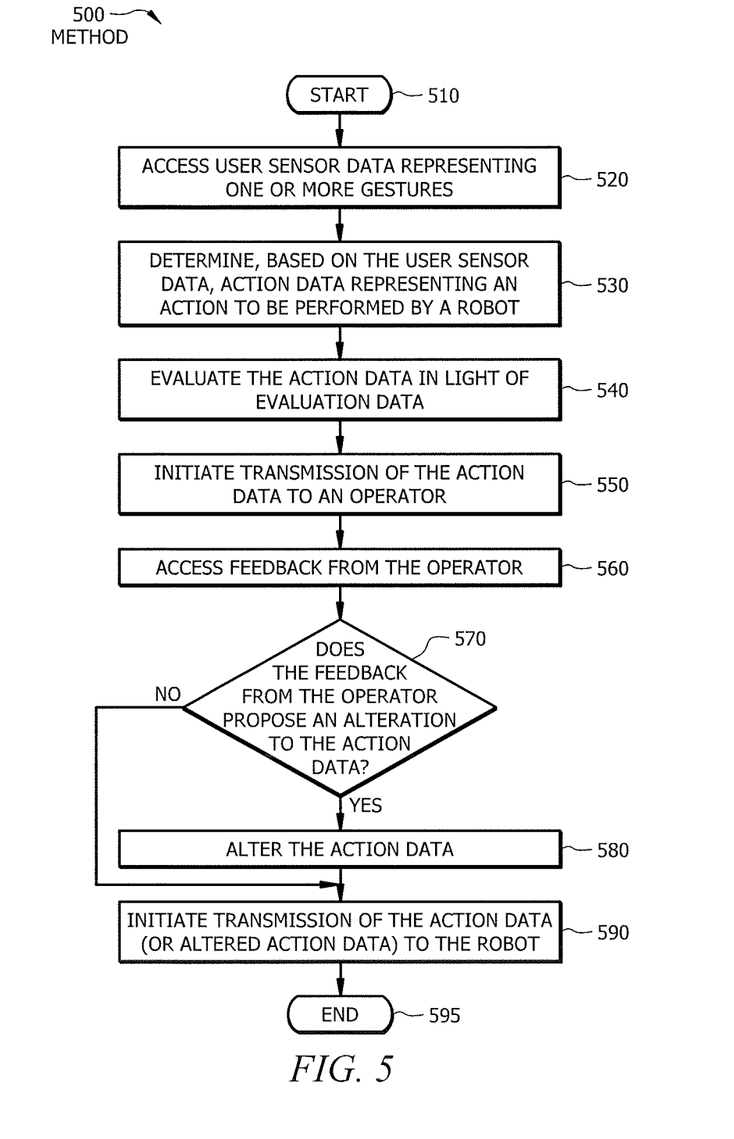
FIG. 5 illustrates an example of a method for determining and evaluating data representing an action to be performed by a robot, according to certain embodiments.

FIG. 5 illustrates an example of a method 500 for determining and evaluating data representing an action to be performed by a robot, according to certain embodiments. The method begins at step 510. At step 520, processor 230 of robot action determiner module 110 accesses user sensor data 262 from user sensor(s) 140. In certain embodiments, user sensor data 262 represents one or more gestures performed by user 150. For example, user sensor data 262 may represent a jabbing gesture performed by user 150. Method 500 may then proceed to step 530.

At step 530, processor 230 of robot action determiner module 110 determines, based on user sensor data 262, action data representing an action to be performed by robot 120. For example, processor 230 may map user sensor data 262 to the action data by associating the one or more gestures performed by user 150 with one or more movements to be performed by robot 120. In certain embodiments, the action data represents a pre-defined set of movements to be performed by robot 120. Method 500 may then proceed to step 540.

At step 540, processor 230 of robot action determiner module 110 evaluates the action data representing the action to be performed by robot 120 in light of evaluation data 270. In certain embodiments, evaluation data 270 includes one or more models 272, historical data 274, or one or more policies 276. Processor 230 may evaluate the action data to be performed by robot 120 by comparing the action data to evaluation data 270. For example, the action data may instruct robot 120 to move a heart during bypass surgery, and processor 230 may compare this action data to a model 272 for moving a heart. Method 500 may then proceed to step 550.

At step 550, processor 230 of robot action determiner module 110 initiates transmission of the action data to operator 132 of computer 130. In certain embodiments, processor 230 initiates transmission of the evaluation data to operator 132 of computer 130. Operator 132 may view the action data on a display of computer 130. In certain embodiments, operator 132 may view the action data overlaid with evaluation data (e.g., model 272) on a display of computer 130. Method may then proceed to step 560.

At step 560, processor 230 of robot action determiner module 110 accesses feedback from operator 132. The feedback from operator 132 may propose an alteration to the action data. For example, the action data may represent an action to be performed by robot 120 of moving a heart two millimeters in a particular direction. Operator 132 may alter this action data to represent an action to be performed by robot 120 of moving a heart three millimeters in a particular direction.

At step 570, processor 230 of robot action determiner module 110 determines whether the feedback from operator 132 proposes an alteration to the action data. If the feedback from operator 132 proposes an alteration to the action data (e.g., moving a heart three millimeters instead of two millimeters), method 500 may proceed to step 580. Otherwise method 500 may proceed to step 590, where processor 230 initiates transmission of the action data to robot 120.

At step 580, processor 230 alters the action data in accordance with the feedback from operator 132. Method 500 may then proceed to step 590, where processor 230 initiates transmission of the altered action data to robot 120. Method 500 ends at step 595.

Modifications, additions, or omissions may be made to method 500 depicted in FIG. 3. Method 500 may include more, fewer, or other steps. For example, at step 580, rather than altering the action data, processor 230 may determine to initiate transmission of the unaltered action data to robot 120. Steps may also be performed in parallel or in any suitable order. While the present disclosure describes particular components as performing particular steps of method 500, the present disclosure contemplates any suitable component of system 100 performing any step of method 500.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A method, comprising:
   accessing, by a processor, sensor input data received from one or more sensors, the sensor input data representing one or more gestures;
   selecting, by the processor and based on the sensor input data representing the one or more gestures, instructions associated with a user from a plurality of instructions associated with multiple users;
   determining, by the processor and based on instructions and the sensor input data representing the one or more gestures, action data representing an action to be performed by a robot, the action comprising physical movements of the robot, and the robot comprises one or more sensors operable to detect motion; and
   evaluating, by the processor, the action data representing the action to be performed by the robot in light of evaluation data.

2. The method of claim 1, further comprising:
   determining, by the processor and based on the evaluation of the action data in light of the evaluation data, to transmit the action data to the robot;
   initiating, by the processor, transmission of the action data to the robot; and
   accessing, by the processor, feedback received from the one or more sensors of the robot, wherein the feedback is based at least in part on the robot performing the action.

3. The method of claim 1, further comprising:
   determining, by the processor and based on the evaluation of the action data in light of the evaluation data, to alter the action data representing the action to be performed by the robot, wherein the altered action data represents a second action to be performed by the robot;
   initiating, by the processor, transmission of the altered action data to the robot; and
   accessing, by the processor, feedback received from the robot, wherein the feedback is based at least in part on the robot performing the second action.

4. The method of claim 1, further comprising:
   initiating, by the processor, transmission of the action data to a computer; and
   accessing, by the processor, feedback received from the computer, wherein the feedback received from the computer is a proposed alteration to the action data representing the action to be performed by the robot;
   altering, by the processor, the action data in accordance with the proposed alteration;
   initiating, by the processor, transmission of the altered action data to the robot; and accessing, by the processor, feedback received from the robot, wherein the feedback received from the robot is associated with the altered action data.

5. The method of claim 1, wherein the evaluation data comprises one or more of the following:
a policy;
a procedural model;
a historical observation;
a vital sign of a patient is a subject of the robot; and
an environmental condition surrounding the robot.

6. The method of claim 1, further comprising:
associating, by the processor, the input data representing the one or more gestures with a profile of the user, wherein:
the one or more gestures are performed by the user; and
determining the action data representing the action to be performed by the robot is based at least in part on the user profile.

7. The method of claim 1, wherein determining, based on the sensor input data representing the one or more gestures, action data representing the action to be performed by the robot comprises mapping the one or more gestures to the action, wherein the action is a pre-defined set of movements to be performed by the robot.

8. One or more computer-readable non-transitory storage media embodying software that is executable to:
access sensor input data received from one or more sensors, the sensor input data representing one or more gestures;
select, based on the sensor input data representing the one or more gestures, instructions associated with a user from a plurality of instructions associated with multiple users;
determine, based on the instructions and the sensor input data representing the one or more gestures, action data representing an action to be performed by a robot, the action comprising physical movements of the robot, and the robot comprises one or more sensors operable to detect motion; and
evaluate the action data representing the action to be performed by the robot in light of evaluation data.

9. The media of claim 8, the media further executable to:
determine, based on the evaluation of the action data in light of the evaluation data, to transmit the action data to the robot;
initiate transmission of the action data to the robot; and
access feedback received from the one or more sensors of the robot, wherein the feedback is based at least in part on the robot performing the action.

10. The media of claim 8, the media further executable to:
determine, based on the evaluation of the action data in light of the evaluation data, to alter the action data representing the action to be performed by the robot, wherein the altered action data represents a second action to be performed by the robot;
initiate transmission of the altered action data to the robot; and
access feedback received from the robot, wherein the feedback is based at least in part on the robot performing the second action.

11. The media of claim 8, the media further executable to:
initiate transmission of the action data to a computer; and
access feedback received from the computer, wherein the feedback received from the computer is a proposed alteration to the action data representing the action to be performed by the robot;
alter the action data in accordance with the proposed alteration;
initiate transmission of the altered action data to the robot; and
access feedback received from the robot, wherein the feedback received from the robot is associated with the altered action data.

12. The media of claim 8, wherein the evaluation data comprises one or more of the following:
a policy;
a procedural model;
a historical observation; and
a vital sign of a patient that is a subject of the robot; and
an environmental condition surrounding the robot.

13. The media of claim 8, the media further executable to:
associate the sensor input data representing the one or more gestures with a profile of the user, wherein:
the one or more gestures are performed by the user; and
determining the action data representing the action to be performed by the robot is based at least in part on the user profile.

14. The media of claim 8, wherein determining, based on the sensor input data representing the one or more gestures, action data representing the action to be performed by the robot comprises mapping the one or more gestures to the action, wherein the action is a pre-defined set of movements to be performed by the robot.

15. A system comprising one or more processors and a memory coupled to the processors comprising instructions executable by the processors to:
access sensor input data received from one or more sensors, the sensor input data representing one or more gestures;
select, based on the sensor input data representing the one or more gestures, instructions associated with a user from a plurality of instructions associated with multiple users;
determine, based on the instructions and the sensor input data representing the one or more gestures, action data representing an action to be performed by a robot, the action comprising physical movements of the robot, and the robot comprises one or more sensors operable to detect motion; and
evaluate the action data representing the action to be performed by the robot in light of evaluation data.

16. The system of claim 15, the instructions further executable to:
determine, based on the evaluation of the action data in light of the evaluation data, to transmit the action data to the robot;
initiate transmission of the action data to the robot; and
access feedback received from the one or more sensors of the robot, wherein the feedback is based at least in part on the robot performing the action.

17. The system of claim 15, the instructions further executable to:
determine, based on the evaluation of the action data in light of the evaluation data, to alter the action data representing the action to be performed by the robot, wherein the altered action data represents a second action to be performed by the robot;
initiate transmission of the altered action data to the robot; and
access feedback received from the robot, wherein the feedback is based at least in part on the robot performing the second action.

18. The system of claim 15, the instructions further executable to:
- initiate transmission of the action data to a computer; and
- access feedback received from the computer, wherein the feedback received from the computer is a proposed alteration to the action data representing the action to be performed by the robot;
- alter the action data in accordance with the proposed alteration;
- initiate transmission of the altered action data to the robot; and
- access feedback received from the robot, wherein the feedback received from the robot is associated with the altered action data.

19. The system of claim 15, wherein the evaluation data comprises one or more of the following:
- a policy;
- a procedural model;
- a historical observation; and
- a vital sign of a patient that is a subject of the robot; and
- an environmental condition surrounding the robot.

20. The system of claim 15, the instructions further executable to:
- associate the sensor input data representing the one or more gestures with a profile of the user, wherein:
- the one or more gestures are performed by the user; and
- determining the action data representing the action to be performed by the robot is based at least in part on the user profile.

* * * * *